United States Patent [19]

Dayton et al.

[11] Plant 3,988

[45] Dec. 14, 1976

[54] APPLE TREE: SIR PRIZE

[75] Inventors: Daniel F. Dayton, Urbana; James B. Mowry, Carbondale, both of Ill.; L. Frederick Hough, Bloomsbury; Catherine Bailey, Englishtown, both of N.J.; Edwin B. Williams, Lafayette, Ind.; Jules Janick; Frank H. Emerson, both of West Lafayette, Ind.; J. Ralph Shay, Corvallis, Oreg.

[73] Assignee: Purdue Research Foundation, West Lafayette, Ind.

[21] Appl. No.: 638,995

[22] Filed: Dec. 8, 1975

[51] Int. Cl.[2] ..... A01H 5/03

[52] U.S. Cl. ..... Plt./34

[58] Field of Search ..... Plt./34

*Primary Examiner*—Robert E. Bagwill
*Attorney, Agent, or Firm*—John R. Nesbitt

EXEMPLARY CLAIM

1. A new and distinct apple tree substantially as shown and described particularly characterized by resistance to apple scab, smooth skin, excellent fresh fruit quality characterized by the ability to maintain quality without shrivelling in storage, and outstanding processing ability, said fruit maturing substantially at the same time as "Golden Delicious".

1 Drawing Figure

1

APPLE TREE: SIR PRIZE

This invention is a new and distinct cultivar of apple tree. It was discovered by applicants in September 1966, at Lafayette, Indiana, in the course of an attempt to develop apple trees with high fruit quality and resistance to *Venturia inaequalis* (cke.) Wint, the causal agent for apple scab disease. The tree is a seedling of known parentage planted in 1955 in Block 9A of the Purdue University O'Neall Memorial Farm, Lafayette, Indiana. In the above orchard its position was Row 8, Tree 121, having the designation 673-20 in applicants' breeding records. This new cultivar is named Sir Prize.

The fruit of Sir Prize resembles Golden Delicious in form and color, but is distinguishable on the basis of its resistance to apple scab and its smoother, waxy skin.

The new cultivar is a seedling, presumably triploid, produced from crossing Doud's Tetraploid (2-4-4) Golden Delicious as the seed parent and a scab resistant seedling 14-152, as the pollen parent. This new variety carries a genetic factor, $V_f$, inherited from *Malus floribunda* 821 which causes it to be resistant to the scab disease caused by *Venturia inaequalis*. The presence of this genetic factor has been repeatedly proven by controlled inoculation tests in the Purdue University greenhouse of both the seedling and its offspring produced from controlled crosses. The complete pedigree is shown below:

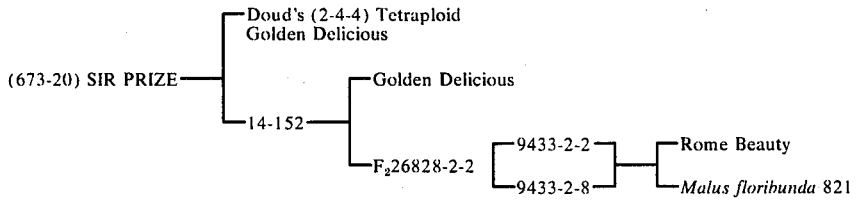

Sir Prize produces a vigorous tree with good annual crops. It is resistant to scab, shows field resistance to fireblight, but may be moderately susceptible to powdery mildew. The tree flowers 2 days before Golden Delicious. The apple fruits have excellent dessert quality which improves in storage. Fruits do not dehydrate after extended storage, however, the skin shows bruise injury more easily than Golden Delicious and bruised or cut surfaces oxidize rapidly.

2

After observing this seedling, the selection was asexually reproduced by grafting on seedling apple roots. The grafted material has maintained the described characteristics after propagation.

The accompanying drawing (color photograph) shows a typical example of the fruit and foliage of Sir Prize.

The following is a detailed description of the new variety with the color designation according to the Horticultural Colour Chart issued by the British Colour Council in collaboration with the Royal Horticultural Society:

FLOWER

Pedicel: 3 cm. (1¼ inches) in length.
Corolla: 5 cm. (2 inches) diameter at anthesis.
Color: Magenta, ranging from plate 27 (tight bud) to 27/3 to paler in open flower.

FRUIT

Shape: Uniform ovate to conic, slightly ribbed.
Size: Axial diameter 7.6 to 8.3 cm. (3 to 3¼ inches) transverse diameter 7.6 to 8.3 cm. (3 to 3¼ inches).
Color: Overall Lemon yellow (plate 4/2); sometimes with a slight, light, red blush.
Skin: Very smooth, waxy with scattered small to medium dots, thin.
Cavity: Acute, medium depth and width, russetted.
Basin: Medium to deep, breadth medium to broad.

Calyx: Persistent closed and recurved.
Calyx tube: Urn-shaped.
Stamens: Basal.
Core lines: Meeting.
Core: Medium, closed, small.
Carpels: Cordate, smooth.
Seeds: Acuminate, not tufted.
Flesh:

*Texture.* — Fine grained, tender, juicy.
*Quality.* — Excellent; sub-acid, rich flavor.
*Color.* — Lemon yellow (plate 4/3).
*Aroma.* — Very pleasant and distinctive.

Maturity Season: Golden Delicious.
Keeping Quality: Very good through entire winter season.
Use: Excellent eating apple.

TREE

Branch: Angles wide and semi-spreading, vigorous, annual bearing.
Foliage: Light green, waxy, smooth and glaborous.

In particular our new variety of apple is distinguished by its resistance to scab, its excellent storage ability, and smooth skin.

We claim:

1. A new and distinct apple tree substantially as shown and described particularly characterized by resistance to apple scab, smooth skin, excellent fresh fruit quality characterized by the ability to maintain quality without shrivelling in storage, and outstanding processing ability, said fruit maturing substantially at the same time as "Golden Delicious".

* * * * *

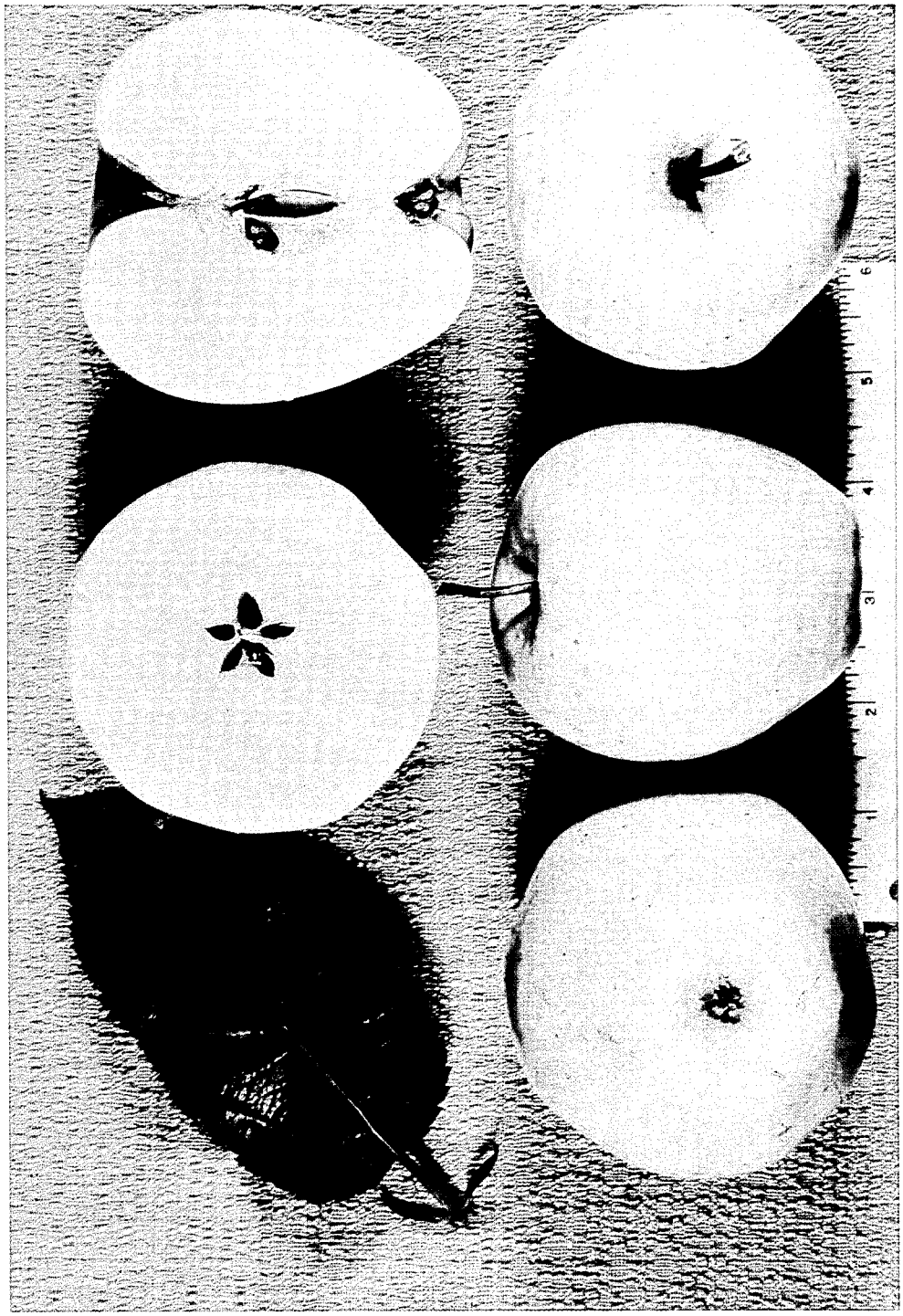

SIR PRIZE
Filed Dec. 8, 1975